United States Patent [19]

Helland

[11] Patent Number: 5,674,273
[45] Date of Patent: Oct. 7, 1997

[54] IMPLANTABLE PACING LEAD WITH CRUSH RESISTANT, PROTECTIVE SLEEVE

[75] Inventor: John R. Helland, Redmond, Wash.

[73] Assignee: Pacesetter, Inc., Sylmar, Calif.

[21] Appl. No.: 543,971

[22] Filed: Oct. 17, 1995

[51] Int. Cl.⁶ ................................................. A61N 4/05
[52] U.S. Cl. ........................ 607/122; 607/126; 604/175
[58] Field of Search ...................... 607/116, 119–132; 128/642, 772; 604/171, 174, 175, 178, 180

[56] References Cited

U.S. PATENT DOCUMENTS

| | | | |
|---|---|---|---|
| 4,553,961 | 11/1985 | Pohndorf et al. | 604/175 |
| 5,107,856 | 4/1992 | Kristiansen et al. | 607/132 X |
| 5,152,298 | 10/1992 | Kreyenhagen et al. | 604/175 X |
| 5,466,253 | 11/1995 | Doan | 607/122 |
| 5,476,493 | 12/1995 | Muff | 607/119 |

Primary Examiner—Jeffrey R. Jastrzab

[57] ABSTRACT

An implantable pacing lead with a reinforcing sheath covering a portion of the lead body to prevent physical stress damage to the lead body. The reinforcing sheath includes a metal coil or ribbon encased in a biocompatible polymer which is positioned about a portion of the lead body.

21 Claims, 2 Drawing Sheets

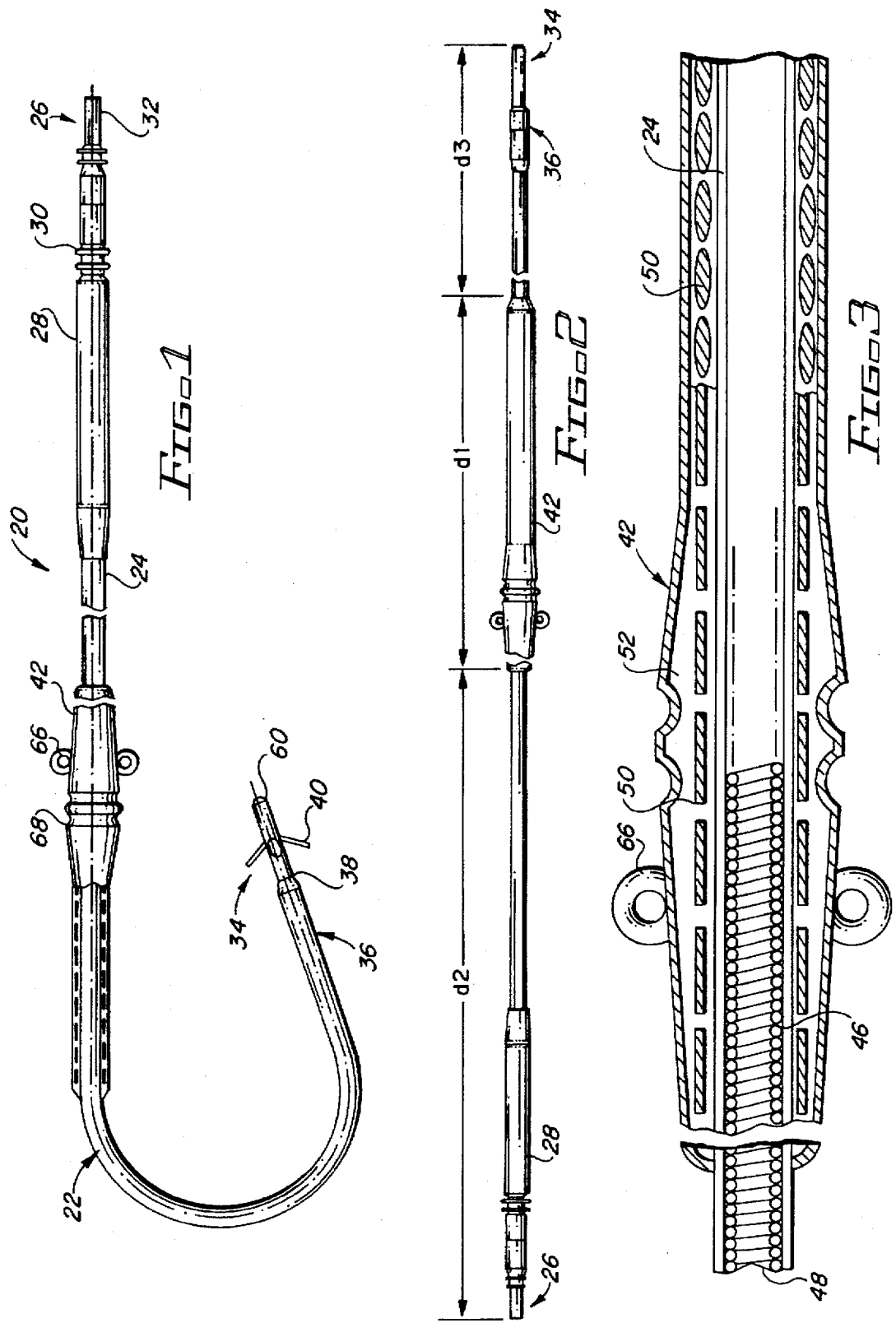

5,674,273

IMPLANTABLE PACING LEAD WITH CRUSH RESISTANT, PROTECTIVE SLEEVE

FIELD OF THE INVENTION

This invention relates generally to an implantable pacing lead for use with a cardiac pacemaker, and, more specifically, to a pacing lead having a reinforced crush resistant sleeve.

BACKGROUND OF THE INVENTION

Current leads used in cardiac stimulation are often implanted transvenously or transthoracically with the result that the lead body can be physically crushed by either bones (i.e. "rib-clavicle" crushing or rib-rib crushing) or by cartilage-rib crushing, etc. and by anchoring sleeves which are tied-down so tightly that the lead body can be crushed and/or damaged. The result of these crushing/constrictive stresses can be severe damage to the insulation, or to the conductors within the lead body, which, in turn, can result in failed conductors and/or failed insulation.

SUMMARY OF THE INVENTION

The present invention utilizes a reinforcing, protective sheath covering a portion of the lead body which prevents the physical stresses noted above from substantially reaching the lead body and causing damage. A metal coil or conduit is wrapped around a portion of the lead body and, in turn, is covered or encased in a biocompatible polymer. The length of this protective sheath is long enough to protect the lead body from a point near the proximal end connector to a point beyond that portion of the lead which would be stressed by bones, ribs, suture sleeves, etc.

DESCRIPTION OF THE DRAWINGS

The above and further features, advantages and benefits of the present invention will be apparent upon consideration of the following detailed description, taken in conjunction with the accompanying drawings, in which like reference characters refer to like parts throughout, and in which:

FIG. 1 shows a plan view of a pacing lead according to the present invention;

FIG. 2 shows a dimensioned view of the lead of FIG. 1;

FIG. 3 shows an enlarged cross-sectional view of the lead body in the area about the fixation sleeve of the lead shown in FIG. 1.

DETAILED DESCRIPTION OF THE PREFERRED EMBODIMENT

Figure 4:
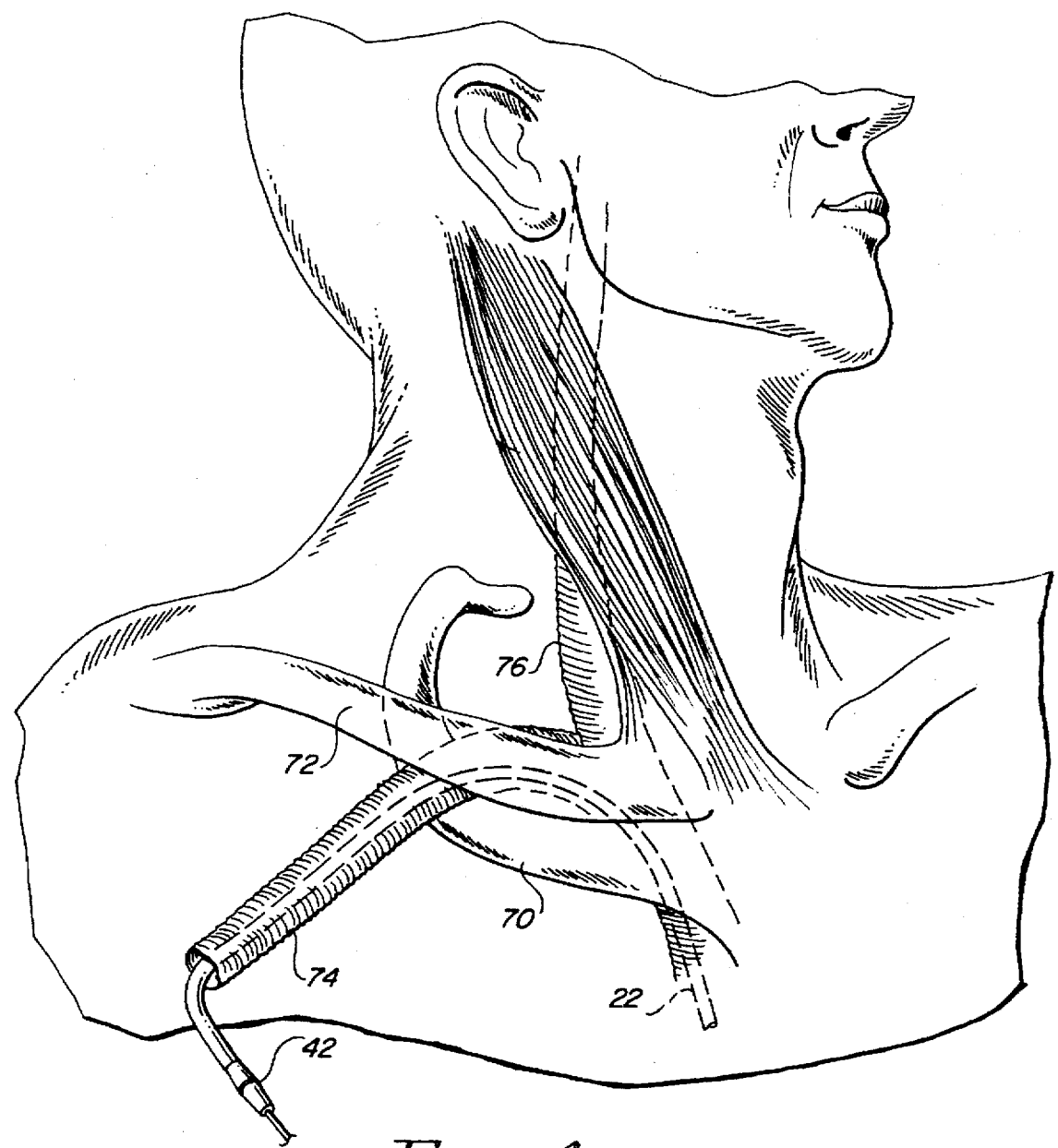
FIG. 4 shows a partially schematic view of the area of venous insertion and the proximate skeletal structure.

FIG. 1 shows a plan view of a pacing lead 20 according to the present invention. The lead 20 is provided with an elongated lead body 22 which includes one or more electrical conductors (FIG. 3) covered with an insulation sheath 24. The insulation sheath is preferably fabricated of silicone rubber, polyurethane or other suitable plastic. At a proximal end 26 of the pacing lead 20 is a connector assembly 28, which is provided with sealing rings 30 and which carries at least one electrical connector pin 32. The connector assembly 28 is constructed using known techniques and is preferably fabricated of silicone rubber, polyurethane or other suitable plastic. Connector pin (or pins) 32 is preferably fabricated of stainless steel or other suitable conductive material.

At a distal end 34 of the pacing lead 20 is an electrode assembly 36. The electrical conductors extend from the proximal end 26 to the distal end 34 of the pacing lead 20, thereby the electrical conductors have a proximal end and a distal end. Immediately behind the distal end of the electrode assembly 36 is a tine sheath 38 which includes a plurality of individual tines 40. Tines 40 engage endocardial tissue and urge the electrode assembly 36 to maintain contact with the endocardium. Tines 40 are more fully described in U.S. Pat. No. 3,902,501, issued to Citron et al., incorporated herein by reference.

A reinforcing means such as a reinforced fixation sleeve 42, which may be either fixed or slidably mounted around lead body 22, serves to stabilize the pacing lead 20 at the site of venous insertion and provide structural support against crushing or constrictive stresses. Accordingly, the relative length of the reinforced fixation sleeve 42 should be long enough to permit fixation by suturing at special fixation areas 66 and 68 near the proximal end 26 of the connector assembly 28 and to extend through and beyond the rib-clavicle area.

The positioning of the fixation sleeve 42 is illustrated in FIG. 2 wherein the length of the fixation sleeve 42 is d1. In the preferred embodiment, the length of d1 is in the range of approximately ten to thirteen (10–13) centimeters, but could be adjusted to account for different body sizes without departing from the spirit of the invention.

It should be noted that the reinforced fixation sleeve 42 may be slidably mounted around the lead body 22.

An enlarged partially cross-sectional, partially cutaway view of a portion of the pacing lead in the area of the reinforced fixation sleeve 42 is illustrated in FIG. 3. The lead body 22 includes at least one electrical conductor 46 which preferably is spiral wound and encased in the insulation sheath 24. The spiral winding of the conductor(s) 46 results in a hollow central area 48, and allows the lead body 22 to remain quite flexible, resulting in a high flexure fatigue resistance. Also, the hollow central area 48 receives an insertion guidewire (not shown) which is relatively stiff and which allows the doctor to guide and control the implantation of the pacing lead 20. Where multiple conductors are required, they may be either coaxially disposed one about the other, or in a side-by-side multi-lumen arrangement.

The construction of the reinforced fixation sleeve 42 is more readily understood upon consideration of FIG. 3. The reinforced fixation sleeve 42 includes a spiral wound ribbon or flat wire 50. The flat wire 50 is encased in a biocompatible polymer covering 52, preferably of similar composition as the insulation sheath 24. The flat wire 50 is not electrically connected to a conductor 46 or electrode of the pacing lead 20. Preferably, the flat wire 50 has a flexural rigidity and tensile strength substantially greater than that of the spiral wound conductor 46. The reinforced fixation sleeve 42 thereby has a higher resistance to compressive or constrictive stresses.

FIG. 4 illustrates the right side neck-shoulder area of a patient. In FIG. 4 the first rib 70 and right clavicle 72 of the skeletal structure are illustrated. As can be seen, the subclavian vein 74 passes between the first rib 70 and right clavicle 72 before merging with the internal jugular vein 76 and proceeding to the heart (not shown). The pacing lead is inserted into the subclavian vein 74, extends through the rib 70–clavicle 72 crossing point and down the jugular vein to the heart (not shown).

The reinforced fixation sleeve 42 is not introduced into the percutaneous lead introducer. However, the reinforced fixation sleeve 42 is long enough to be ultimately implanted and positioned to extend through and beyond the rib-clavicle area in a subclavian vein transvenous implant (see FIG. 4). The reinforced fixation sleeve 42 also extends to the point of and may provide a special fixation area 66 (FIG. 3) for suture tie down anchoring. Alternatively, the reinforced fixation sleeve 42 may be configured to cover the lead body 22 at and around the portion which courses through the ribs in a transthoracic-myocardial lead.

In the preferred embodiment, the diameter of the lead body is in the range of between about 1.50 mm and 2.50 mm and preferably about 2.0 mm, while the diameter of the reinforced fixation sleeve 42 is in the range of 2.0 mm to 5.0 mm and preferably about 3.0 mm to 4.0 mm. When the flat wire 50 has a flattened oval cross-sectional shape, as illustrated at the right in FIG. 3, the flat wire 50 preferably has a minor diameter in the range of between about 0.05 mm and 1.0 mm and a major diameter in the range of between about 0.2 mm and 5.0 mm, preferably having the dimensions of 0.25 mm by 0.75 mm. Alternatively, where the flat wire 50 has a rectangular ribbon configuration as shown at the left of FIG. 3, the thickness would be in the range of between about 0.05 mm and 1.0 mm, while the width would be in the range of between about 0.2 mm and 5.0 mm, preferably having the dimensions 0.25 mm by 0.75 mm.

The flat wire 50 is preferably a material selected from such materials as: a nickel-cobalt-molybdenum alloy, an iron-nickel-cobalt-molybdenum alloy, titanium, and other similar metals, or alloys including additional minor components. It may also be made up of composites, for example, nickel-cobalt-molybdenum alloy in combination with titanium or silver or other suitable materials in the core or on the surface to add strength or other desirable attributes. Materials for the flat wire 50 are selected based on their high tensile strength, fatigue and corrosion resistance and resistivity.

It should be evident from the foregoing description that the present invention provide advantages over pacing leads of the prior art. Although preferred embodiments are specifically illustrated and described herein, it will be appreciated that many modifications and variations of the present invention are possible in light of the above teaching to those skilled in the art. It is preferred, therefore, that the present invention be limited not by the specific disclosure herein, but only by the appended claims.

What is claimed is:

1. An implantable pacing lead for use with a cardiac pacemaker, comprising:

a lead body having a proximal end and a distal end, the lead body having at least one electrical conductor and an insulation sheath covering the at least one electrical conductor;

an electrical connector coupled to the proximal end of the at least one electrical conductor;

an electrode coupled to the distal end of the at least one electrical conductor; and reinforcing sleeve means for preventing crushing forces from damaging the at least one electrical conductor, the reinforcing sleeve means including a spiral wound length of stress resistant material encased in a biocompatible polymer material.

2. The implantable pacing lead of claim 1, wherein the reinforcing sleeve means comprises:

means for suturing the reinforcing sleeve means to body tissue, the suturing means having at least one suture groove, the spiral wound length of stress resistant material being extended beneath the suture groove to prevent excessive tie down forces from damaging the at least one electrical conductor.

3. The implantable pacing lead of claim 1, wherein the reinforcing sleeve means comprises:

a protective sheath of the stress resistant material, the sheath being long enough to protect the lead body from a point near the proximal electrical connector to a point beyond that portion of the lead which would be stressed by bones, or other constrictive tissue.

4. The implantable pacing lead of claim 1, wherein the spiral wound length of stress resistant material of the reinforcing sleeve means further comprises:

a flattened oval cross section wire having a minor diameter in the range of between about 0.05 mm and 1.0 mm, and a major diameter in the range of between about 0.2 mm and 5.0 mm.

5. The implantable pacing lead of claim 1, wherein the spiral wound length of stress resistant material of the reinforcing sleeve means further comprises:

a rectangular ribbon shaped wire having a thickness in the range of between about 0.05 mm and 1.0 mm, and a width in the range of between about 0.2 mm and 5.0 mm.

6. The implantable pacing lead of claim 1, wherein the spiral wound length of stress resistant material of the reinforcing sleeve means is a material selected from the group consisting of nickel-cobalt-molybdenum alloy, iron-nickel-cobalt-molybdenum alloy, titanium, and a composite of nickel-cobalt-molybdenum with a silver core.

7. The implantable pacing lead of claim 1, wherein the insulation sheath covering the electrical conductor has a diameter in the range of between about 1.50 mm and 2.50 mm and the reinforcing sleeve means has a diameter in the range of between about 2.0 mm to 5.0 mm.

8. An implantable pacing lead for use with a cardiac pacemaker, comprising:

a lead body having a proximal end and a distal end, the lead body having at least one electrical conductor and a flexible insulation sheath covering the at least one electrical conductor;

an electrical connector affixed to the proximal end of the electrical conductor;

an electrode assembly affixed to the distal end of the electrical conductor; and a flexible reinforcing sheath disposed annularly about the proximal end of the lead body, the reinforcing sheath having means for suturing the reinforcing sheath to body tissue, the reinforcing sheath further being highly resistant to compressive and constrictive forces.

9. The implantable pacing lead of claim 8, wherein the reinforcing sheath has a length of about 10 to 13 centimeters.

10. The implantable pacing lead of claim 8, wherein the reinforcing sheath comprises:

a spiral wound extended length of high tensile strength, fatigue and corrosion resistant material; and a biocompatible polymer material encasing the spiral wound extended length of high tensile strength, fatigue and corrosion resistant material.

11. The implantable pacing lead of claim 10, wherein the spiral wound extended length of high tensile strength, fatigue and corrosion resistant material of the reinforcing sheath further comprises:

a flattened oval cross section wire having a minor diameter in the range of between about 0.05 mm and 1.0 mm, and a major diameter in the range of between about 0.2 mm and 5.0 mm.

12. The implantable pacing lead of claim 11, wherein the insulation sheath covering the electrical conductor has a diameter in the range of between about 1.50 mm and 2.50 mm and the reinforcing sheath has a diameter in the range of between about 2.0 mm to 5.0 mm.

13. The implantable pacing lead of claim 10, wherein the spiral wound extended length of high tensile strength, fatigue and corrosion resistant material of the reinforcing sheath further comprises:

a rectangular ribbon shaped wire having a thickness in the range of between about 0.05 mm and 1.0 mm, and a width in the range of between about 0.2 mm and 5.0 mm.

14. The implantable pacing lead of claim 10, wherein the spiral wound extended length of high tensile strength, fatigue and corrosion resistant material of the reinforcing sheath is a material selected from the group consisting: of nickel-cobalt-molybdenum alloy, iron-nickel-cobalt-molybdenum alloy, titanium, and a composite of nickel-cobalt-molybdenum with a silver core.

15. An implantable pacing lead for use with a cardiac pacemaker, comprising:

a lead body having a proximal end and a distal end, the lead body having at least one electrical conductor and an insulation sheath covering the at least one electrical conductor;

an electrical connector coupled to the proximal end of the at least one electrical conductor;

an electrode coupled to the distal end of the at least one electrical conductor; and a flexible crush-resistant protective sleeve having means for preventing bones, or other constrictive tissue or tie-downs, from damaging the electrical conductor, the protective sleeve being disposed annularly about the proximal end of the lead body and slidably positioned to protect the lead body from a point near the electrical connector to a point beyond that portion of the lead body which would be stressed by bones, or other constrictive tissue or tie-downs.

16. The implantable pacing lead of claim 15, wherein the protective sleeve comprises:

a spiral wound length of stress resistant material; and a biocompatible polymer material encasing the spiral wound length of stress resistant material.

17. The implantable pacing lead of claim 16, wherein the protective sleeve further comprises:

means for suturing the protective sleeve to body tissue, the spiral wound length of stress resistant material being extended beneath the suturing means to prevent excessive tie down forces from damaging the at least one electrical conductor.

18. A reinforced fixation sleeve for use with a cardiac pulse generator pacing lead body, the lead body having at least one electrical conductor, the fixation sleeve comprising an inner surface defining a lumen for receiving the lead body, the fixation sleeve comprising a biocompatible polymer material, the fixation sleeve further having reinforcing means for preventing crushing forces from damaging the at least one electrical conductor, the reinforcing means including a spiral wound length of stress resistant material encased in the biocompatible polymer material.

19. The reinforced fixation sleeve of claim 18, wherein the reinforcing means comprises:

means for suturing the reinforcing means to body tissue, the suturing means comprising at least one suture groove on the fixation sleeve, the spiral wound length of stress resistant material being extended beneath the suture groove to prevent excessive tie down forces from damaging the at least one electrical conductor.

20. The reinforced fixation sleeve of claim 18, wherein the spiral wound length of stress resistant material of the reinforcing means further comprises:

a flattened oval cross section wire having a minor diameter in the range of between about 0.05 mm and 1.0 mm, and a major diameter in the range of between about 0.2 mm and 5.0 mm.

21. The reinforced fixation sleeve of claim 18, wherein the spiral wound length of stress resistant material of the reinforcing means further comprises:

a rectangular ribbon shaped wire having a thickness in the range of between about 0.05 mm and 1.0 mm, and a width in the range of between about 0.2 mm and 5.0 mm.

* * * * *